(12) United States Patent
Fitzsimmons et al.

(10) Patent No.: US 6,493,078 B1
(45) Date of Patent: Dec. 10, 2002

(54) METHOD AND APPARATUS TO IMPROVE COATING QUALITY

(75) Inventors: John A. Fitzsimmons, Poughkeepsie, NY (US); Darryl D. Restaino, Modena, NY (US); Michael J. Schade, Hopewell Junction, NY (US)

(73) Assignee: International Business Machines Corporation, Armonk, NY (US)

( * ) Notice: Subject to any disclaimer, the term of this patent is extended or adjusted under 35 U.S.C. 154(b) by 0 days.

(21) Appl. No.: 09/956,367

(22) Filed: Sep. 19, 2001

(51) Int. Cl.[7] .............................................. G01N 21/00
(52) U.S. Cl. ................ 356/239.7; 356/237.1; 356/237.3
(58) Field of Search .................. 356/239.7, 239.8, 356/237.1, 237.2, 237.3, 237.4, 237.5, 601, 630, 614; 118/723, 725; 427/9–10, 240, 385.5; 250/559.41

(56) References Cited

U.S. PATENT DOCUMENTS

| | | | |
|---|---|---|---|
| 4,647,172 A | | 3/1987 | Batchelder et al. |
| 4,851,311 A | | 7/1989 | Millis et al. |
| 5,244,501 A | * | 9/1993 | Nakayama et al. ......... 118/725 |
| 5,366,757 A | * | 11/1994 | Lin ............................... 427/9 |
| 5,653,811 A | * | 8/1997 | Chan ........................... 118/723 |
| 5,843,527 A | | 12/1998 | Sanada |
| 5,940,175 A | | 8/1999 | Sun |
| 5,962,193 A | * | 10/1999 | Lin et al. ..................... 427/240 |
| 5,985,357 A | | 11/1999 | Sanada |
| 5,995,218 A | | 11/1999 | Ide |

FOREIGN PATENT DOCUMENTS

| | | | |
|---|---|---|---|
| JP | 61201107 A | | 9/1986 |
| JP | 62008525 A | | 1/1987 |
| JP | 04 167 525 | * | 6/1992 |
| JP | 05 047 673 | * | 2/1993 |
| JP | 9082608 A | | 3/1997 |

* cited by examiner

Primary Examiner—Frank G. Font
Assistant Examiner—Sang H. Nguyen
(74) Attorney, Agent, or Firm—Steven Capella

(57) ABSTRACT

A method and structure for improving a coating on a substrate comprises a chamber further comprising a rotatable holder, which holds the substrate; a supply of coating material for coating the substrate in the chamber; a window in the wall of the chamber; and a supply of liquid for coating at least a portion of the window on the interior side of the chamber. The chamber is preferably adapted to house the window in multiple configurations. A camera (or other optical detector), which is positioned outside of the chamber, monitors the substrate through the window.

19 Claims, 4 Drawing Sheets

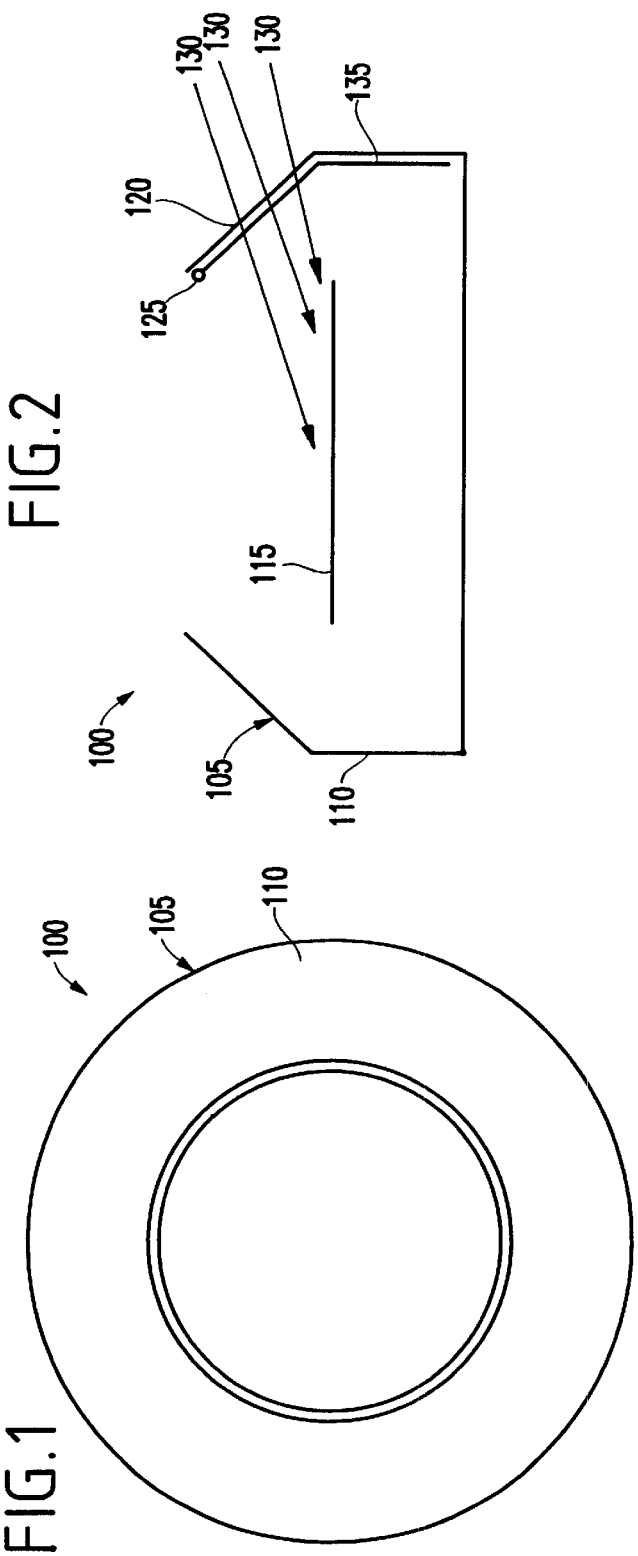

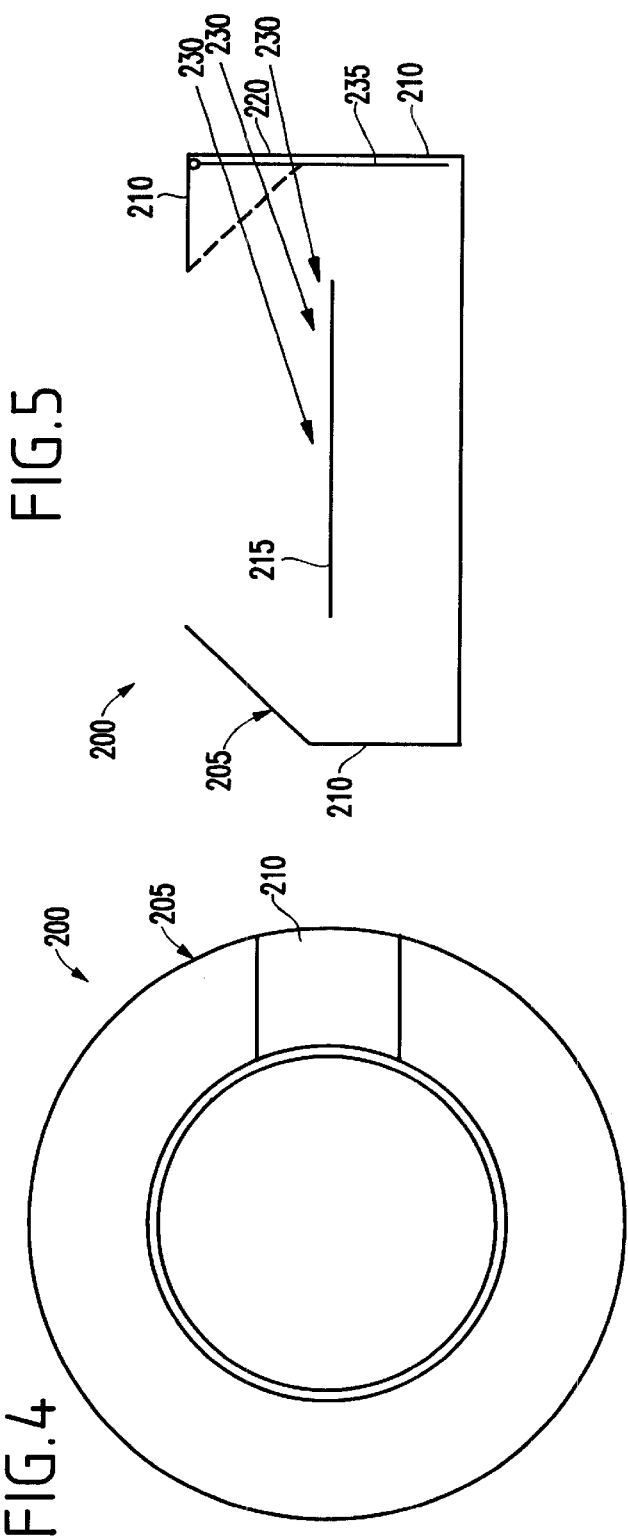
FIG.4
FIG.5
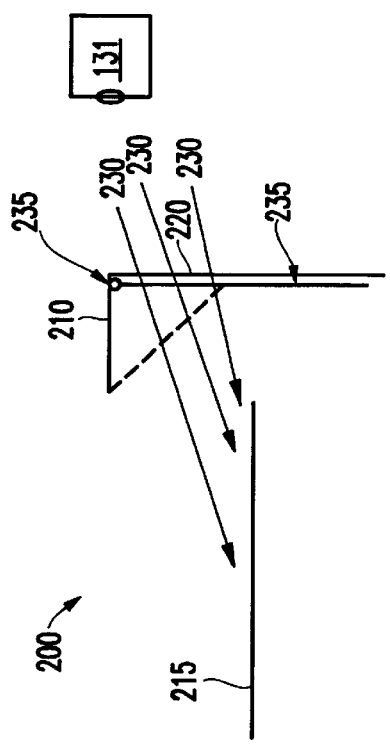
FIG.6

METHOD AND APPARATUS TO IMPROVE COATING QUALITY

BACKGROUND OF THE INVENTION

1. Field of the Invention

The present invention generally relates to equipment used for inspecting defects in semiconductor devices, and more particularly to a method and apparatus to observe and inspect coating defects in semiconductor wafers and to improve the quality of such coatings.

2. Description of the Related Art

Conventional spin-on coating processes are used in semiconductor manufacturing to deposit several layers on semiconductor substrates. Usually, a single-crystal silicon wafer is used in integrated circuit manufacturing. Additionally, spin-on coating processes are capable of being used in processes where the substrate to be coated does not exhibit a high degree of crystallinity.

Furthermore, coating materials applied by spin-coating processes include several types of materials such as 1) dopant containing materials which are subjected to post deposition treatment, such as heat treatment, to diffuse a dopant into a semiconductor substrate for forming, for example, a p-n diode junction therein; or 2) materials which, upon post-deposition treatment, form anti-reflective layers; or 3) electrically conductive materials for forming transparent or opaque electrodes or contacts; or 4) dielectric materials used as insulator layers, protective coatings, and gap-fill and damascene style metallization process materials; or 5) photoresist materials used in photolithographic or other types of selective patterning processing as by chemical or physical etching.

For example, a conventional spin-on coating technique of a dielectric material involves preparing a fluid consisting of the coating material dissolved, dispersed, or suspended in a suitable volatile solvent or other vehicle, along with any other process or product enhancing additive; dispensing an amount of the fluid on a substrate; i.e., a semiconductor wafer; and spinning the wafer with a rotational speed sufficient to spread the coating fluid in a uniform thickness over at least the portion of the wafer intended to be coated. The rotational speed, surface tension, and viscosity of the coating fluid generally determine the thickness of the resulting coating. Following spin-on deposition, the deposited film is cured at an elevated temperature and for a time sufficient to obtain a dielectric film having the desired properties.

Due to the submicron size of the devices involved and the speed of manufacturing, it is no surprise that defects arise in the spin-on coatings. However, the quality of the semiconductor substrate can vastly improve by detecting these defects, and curing them prior to further manufacturing, sale, and use of the device.

The evaluation of semiconductor wafer edges is a fundamental concern in quality control analysis in semiconductor manufacturing. The evaluation at the edge of the wafer is often times more critical to the production of high quality film coatings than other locations of the wafer because of the propensity of defects occurring near the edge of the wafer. These defects have many possible causes such as insufficient shot size, foreign material contamination, and non-uniform material build up. Most defect detection systems are not integrated with the deposition tool, especially spin-on deposition equipment because of the difficulty of maintaining a clear optical train between the wafer surface and the detector sensor.

High quality film coatings are a necessity to ensure a high quality semiconductor wafer and device. Many film coatings are applied by spin-on application techniques and often these coatings contain defects, and in order to remove the defects, a thorough defect detection system should be used. Poor quality coatings have a major impact on film quality, which in turn drives increased manufacturing costs due to the required rework necessary to achieve a high quality coating. Therefore, there is a need to improve the inspection capabilities of wafer detection systems in order to provide higher quality coatings, and an overall better quality semiconductor device.

SUMMARY OF THE INVENTION

In view of the foregoing and other problems, disadvantages, and drawbacks of the conventional wafer inspection and defect detection systems, the present invention has been devised, and it is an object of the present invention to provide an apparatus and method for detecting defects in semiconductor wafers by providing an inspection apparatus, which closely monitors the wafer including the edge region.

In order to attain the object suggested above, there is provided, according to one aspect of the invention a structure and method for improving a coating on a substrate, the structure further comprising a chamber further comprising a holder, which holds the substrate; a supply of a coating material for coating the substrate in the chamber; a window in the wall of the chamber; and a supply of liquid for coating at least a portion of the window on the interior side of the chamber. The chamber is preferably adapted to house the window in multiple configurations. A camera, or other optical detector (s), which is positioned outside of the chamber, monitors the substrate through the window. Furthermore, the holder for the substrate rotates during the coating process.

In another aspect, the present invention encompasses methods using a wet window technique, wherein a flowing solvent in a laminar flow region is used to wet the surface and the optical window in order to intercept and remove contamination before it can impinge and stick to the optical window. If contaminants stick or attach to the optical window, they can obstruct the observation of the wafer, thus making the wafer quality determination difficult. The wet window does not introduce significant degradation of the optical signal because it is a substantially uniform film of liquid which gently flows over the window, much like adding on additional optical window only. This window is liquid rather than a typical solid window associated with conventional optical windows. The physical solid window acts as a uniform support for this liquid window.

The solid support window is preferably smooth enough that it does not introduce turbulence into the liquid flowing over the window, and it preferably does not have a significant solubility or chemical interaction with the liquid window.

The liquid window is preferably formed from a liquid that does not introduce a significant refraction that cannot be corrected by optical or electronic techniques; and the liquid is preferably a solvent for the contamination (resist, or other organic film spin-on the wafer), which would normally occlude the solid optical window, to a sufficient extent that this contamination would not build up and occlude or interfere significantly with the optical train.

In another aspect, the invention encompasses an apparatus and method involving the real-time defect detection feedback to avoid large amounts of product to be processed before the defect is observed and corrective action is taken. While the present technique is particularly suited for evaluation of the edge of a wafer, it can be applied to the total wafer as well, and thus maximize the percentage of defect corrected.

BRIEF DESCRIPTION OF THE DRAWINGS

The foregoing and other objects, aspects and advantages will be better understood from the following detailed description of a preferred embodiment of the invention with reference to the drawings, in which:

FIG. 1 is a top view of a first embodiment of a defect detection system;

FIG. 2 is a front view of a first embodiment of the defect detection system shown in FIG. 1;

FIG. 3 is an alternate front view of a first embodiment of the defect detection system shown in FIG. 1;

FIG. 4 is a top view of a second embodiment of a defect detection system;

FIG. 5 is a front view of a second embodiment of the defect detection system shown in FIG. 4;

FIG. 6 is an alternate front view of a second embodiment of the defect detection system shown in FIG. 4;

DETAILED DESCRIPTION OF PREFERRED EMBODIMENTS OF THE INVENTION

Figure 8:
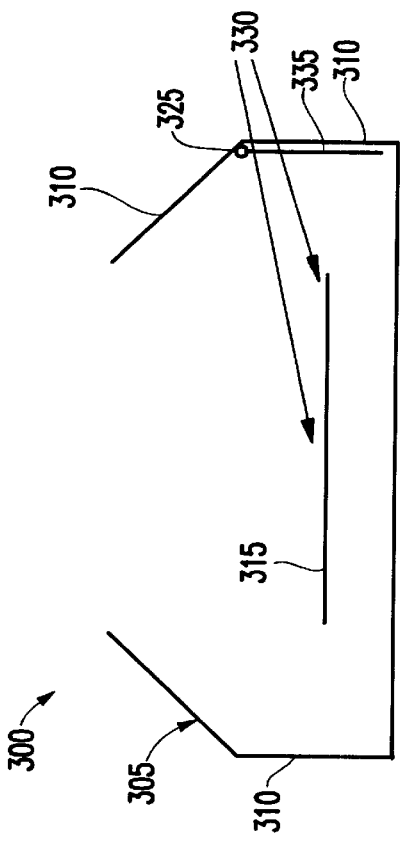
FIG. 8 is a front view of a third embodiment of the defect detection system shown in FIG. 7.

As previously mentioned, there is a need to improve the quality of wafer coatings in semiconductor manufacturing processes especially in a real time feedback mode. This will enable less rework of the product because any problems will be detected early and repaired before large amounts of poor quality products are produced. Accordingly, in order to do so, an improved defect detection system is disclosed to better evaluate wafers, including the edge region, in a real time manner, thereby improving overall coating quality and minimizing the amount or quantity of poor quality coating requiring rework. Although the present invention deals mainly with spin-on coating application techniques, it can conceptually be applied to any technique using a solution dispenser for film application to a substrate, for example, but not limited, to other methods such as spray and doctor blade application techniques.

The present invention utilizes a technique whereby a device such as a camera is used to observe the area of the substrate most probable to have defects which result in the need for coating rework. This camera may be assisted with a constant illumination or a stroboscopic flash device using a wavelength or wavelengths which are not actinic to the film of interest. Therefore, this light will not be a source of defects due to undesirable photochemical interaction. The method to produce this non-actinic light may be any known in the art such as filters to limit undesirable emission, specific radiation sources using qualified wavelengths such as solid state diodes, or combinations of several methods.

The illumination device is utilized to enhance resolution of the camera to detect coating defects. Stop-action imaging may be used by either a timed pulse to synchronize the camera frame grabber or by use of a stroboscopic flash. These methods would enable real-time feedback to improve coating operations or act as a detector to limit processing when undesired results are observed as well as interface with the operator of the coating tool to identify an undesired condition. Both of these actions have direct consequences in decreasing multiple wafers with coating defects, with the direct result being that there are less requirements to repair multiple poor quality coatings on wafers.

The selectable wavelength used for the camera maximizes the overall defect detection, and minimizes the film change due to its non-actinic properties. The illumination by a lamp/diode array allows for multiple wavelength selection, and provides a monochromatic light source without causing additional defects through photo chemical reactions. Moreover, this type of illumination maximizes the sensitivity to the particular film type, and enables multiple film types to be evaluated with very high sensitivity. Due to the type of light used and its corresponding wavelength, very thin coatings may be observed. In fact, the silicon substrate acts as a mirror, thereby providing a reflective measurement quality to the overall process.

The placement of the camera is preferably such that a clear image of the wafer could be captured. This requires a direct line-of-sight positioning of the camera with respect to the wafer. One problem that must be overcome is that the natural spin-off of excess coating material will quickly coat the camera lens, making it unable to detect the wafer. This is solved with the invention by placing the camera behind a transparent window built into the existing coater bowl. The transparent window is kept clean by making use of a flowing solvent stream directed at the window. Alternatively, if the camera is sufficiently sealed, the solvent can be directly applied to the camera lens, thereby avoiding the need for a transparent window. For example, spin-on coatings of SILK® (low dielectric constant insulator sold by the Dow Chemical Company) make use of PGMEA (Propylene Glycol Methyl Ether Acetate) solvent to keep the coater bowls clean. Other solvents which may be used are mesitylene, cyclohexane, and GBL mixtures.

The solvent is defined by the optical wavelength for inspection, the solubility for the contamination, and the compatibility with the solid window materials. Thus, the laminar flow of the solvent gives a more uniform solvent liquid thickness, thus the window refrains from becoming blurry or hazy. For optimum detection capability, the window solvent stream needs to be applied during the critical stages of spin-on coating so that the wet window remains clean. Despite the potential for the coater bowl solvent stream to interfere with the drying properties of the wafer film coating, the present invention is configured such that no detrimental effect upon film quality occurs. This process occurs by keeping the window solvent stream directed away from the wafer, and using adequate bowl exhaust to prevent solvent stream fumes from affecting the drying properties of the film coating.

Types of signals which are useful in observing are: 1) the fringe pattern of drying films; 2) the star-burst pattern of a short-shot wafer due to inadequate chemical dispensing; 3) pull-back of a film from the wafer's edge subsequent to the coating completion; and 4) the quality of the edge bead removal. Problems with any of these issues can lead to process rework, or even worse, wafer scrapping if the defect goes undetected. A particularly bad example would involve inadequate dispensing of the adhesion promoter for SILK®. Because the adhesion promoter is very thin and is covered by the SILK® coating, any problems with this adhesion promoter coating would not be detected until much later in the semiconductor wafer processing when it is far too late to rework the wafer. This is a particularly significant advantage, as the rework of this adhesion promotion layer is quite complex and it is much more advantageous to avoid multi wafers with problems. The real time advantage of the present techniques minimize multiple bad wafers.

The present invention preferably utilizes a digital camera to observe the edge of a spinning wafer during coating or directly after coating to detect poor coatings that may arise from insufficient shot-size or lack of adhesion to the edge of the wafer. However, as previously mentioned, any camera, monitor, or viewer known in the art may be used.

Referring now to the drawings, and more particularly to FIGS. 1 through 3, there are shown schematics of a first embodiment of a structure according to the present invention. In FIG. 1, there is shown a top view of an apparatus 100 for improving the coating quality of a substrate. The apparatus 100 comprises a chamber 105 embodied as a coater bowl 105 comprising a wall 110. FIGS. 2 and 3 further illustrate the first embodiment, wherein the apparatus 100 is shown in a cross-sectional view and further comprises a substrate 115 disposed in the chamber 105. A window 120 is shown disposed in the wall 110 of the chamber 105. In the first embodiment, the window 120 is disposed in the angled portion of the wall 110 of the chamber 105.

A wet window dispense port 125 is shown at the upper portion of the window 120 to provide a laminar flowing liquid coating 135 on the transparent window 120. The flow of the liquid coating 135 is preferably adjusted such that the flow remains laminar, and just wets the surface of the window 120. Multiple dispense ports may be used, or a fine continuous slot may be used for the dispense nozzle 125. A line of sight 130 for a camera 131 is also provided, such that the line of sight 130 extends from the camera 131 through the window 120, and onto the substrate 115. The line of sight allows for views extending from the edge of the wafer continuing to the upper surfaces of the wafer, as indicated. The substrate 115 is held in the chamber 105 by a rotating holder (not shown). The chamber 105 is preferably adapted to house the window 120 in multiple configurations, such as at an angled position as depicted in the first embodiment, and at other positions as shall be discussed in several other embodiments.

In FIGS. 4 through 6, a second embodiment of a structure according to the present invention is illustrated. In FIG. 4, there is shown an apparatus 200 for improving the coating quality of a substrate. The apparatus 200 comprises a chamber 205 embodied as a coater bowl 205 comprising a wall 210. FIGS. 5 and 6 further illustrate the second embodiment, wherein the apparatus 200 is shown further comprising a substrate 215 disposed in the chamber 205. A window 220 is shown disposed in the wall 210 of the chamber 205. In the second embodiment, the window 220 is disposed in the straight vertical portion of the wall 210 of the chamber 205. For contrast, the position where the angled portion of the wall 110 (from the previous embodiment) would be is shown as a dashed line.

A wet window dispense port 225 is shown at the upper portion of the window 220 to provide a laminar flowing liquid coating 235 on the transparent window 220. The flow of the liquid coating 235 is preferably adjusted such that the flow remains laminar, and just wets the surface of the window 220. Multiple dispense ports 225 may be used, or a fine continuous slot may be used for the dispense nozzle 225. Moreover, a line of sight 230 for a camera 131 is provided, such that the line of sight 230 extends from the camera 131 through the window 220, and onto the substrate 215. The line of sight allows for views extending from the edge of the wafer continuing to the upper surfaces of the wafer, as indicated. As with the first embodiment, the substrate 215 is held in the chamber 205 by a rotating holder (not shown).

Figure 7:
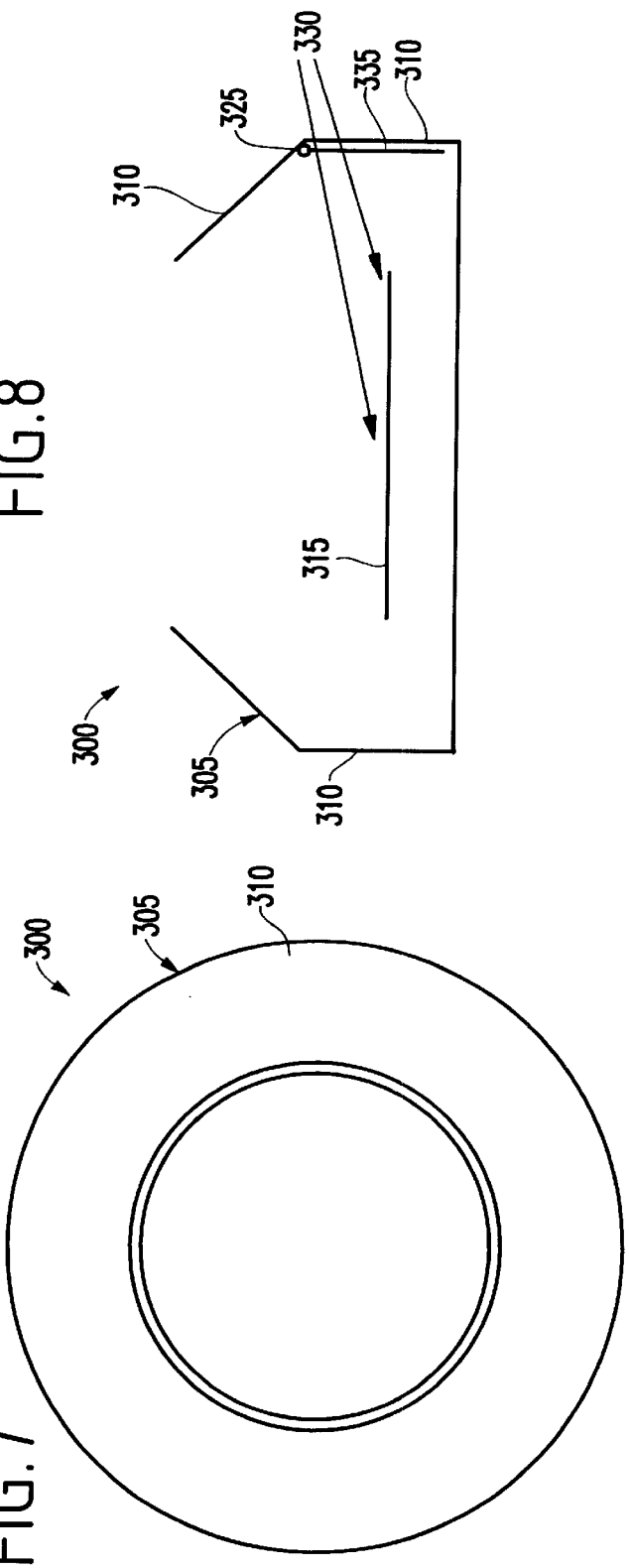
FIG. 7 is a top view of a third embodiment of a defect detection system.
Figure 9:
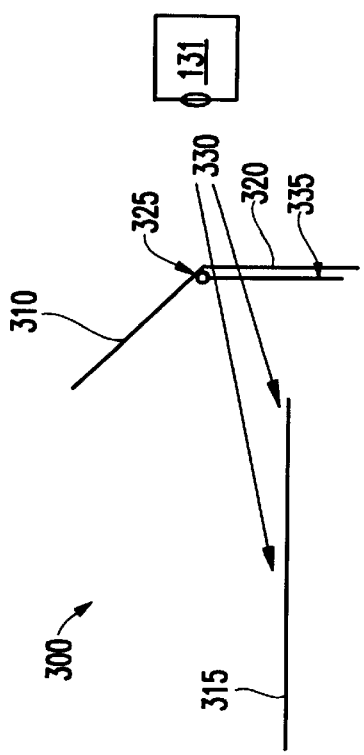
FIG. 9 is an alternate front view of a third embodiment of the defect detection system shown in FIG. 7.

FIGS. 7 through 9 show a third embodiment of a structure according to the present invention. In FIG. 7, an apparatus 300 is shown for improving the coating quality of a substrate. The apparatus 300 comprises a chamber 305 embodied as a coater bowl 305 further comprising a wall 310. FIGS. 8 and 9 further illustrate the third embodiment, wherein the apparatus 300 is shown further comprising a substrate 315 disposed in the chamber 305. A window 320 is shown disposed in the wall 310 of the chamber 305. In the third embodiment, the window 320 is disposed in the straight vertical portion of the wall 310 of the chamber 305 beginning at the point where the wall 310 begins to angle up.

A wet window dispense port 325 is shown at the upper portion of the window 320 to provide a laminar flowing liquid coating 335 on the transparent window 320. The flow of the liquid coating 335 is preferably adjusted such that the flow remains laminar, and just wets the surface of the window 320. Multiple dispense ports may be used, or a fine continuous slot may be used for the dispense nozzle 325. Moreover, a line of sight 330 for a camera 131 is provided, such that the line of sight 330 extends from the camera 131 through the window 320, and onto the substrate 315. The line of sight allows for views extending from the edge of the wafer continuing to the upper surfaces of the wafer, as indicated. As with the first and second embodiments, the substrate 315 is held in the chamber 305 by a rotating holder (not shown).

Figure 10:
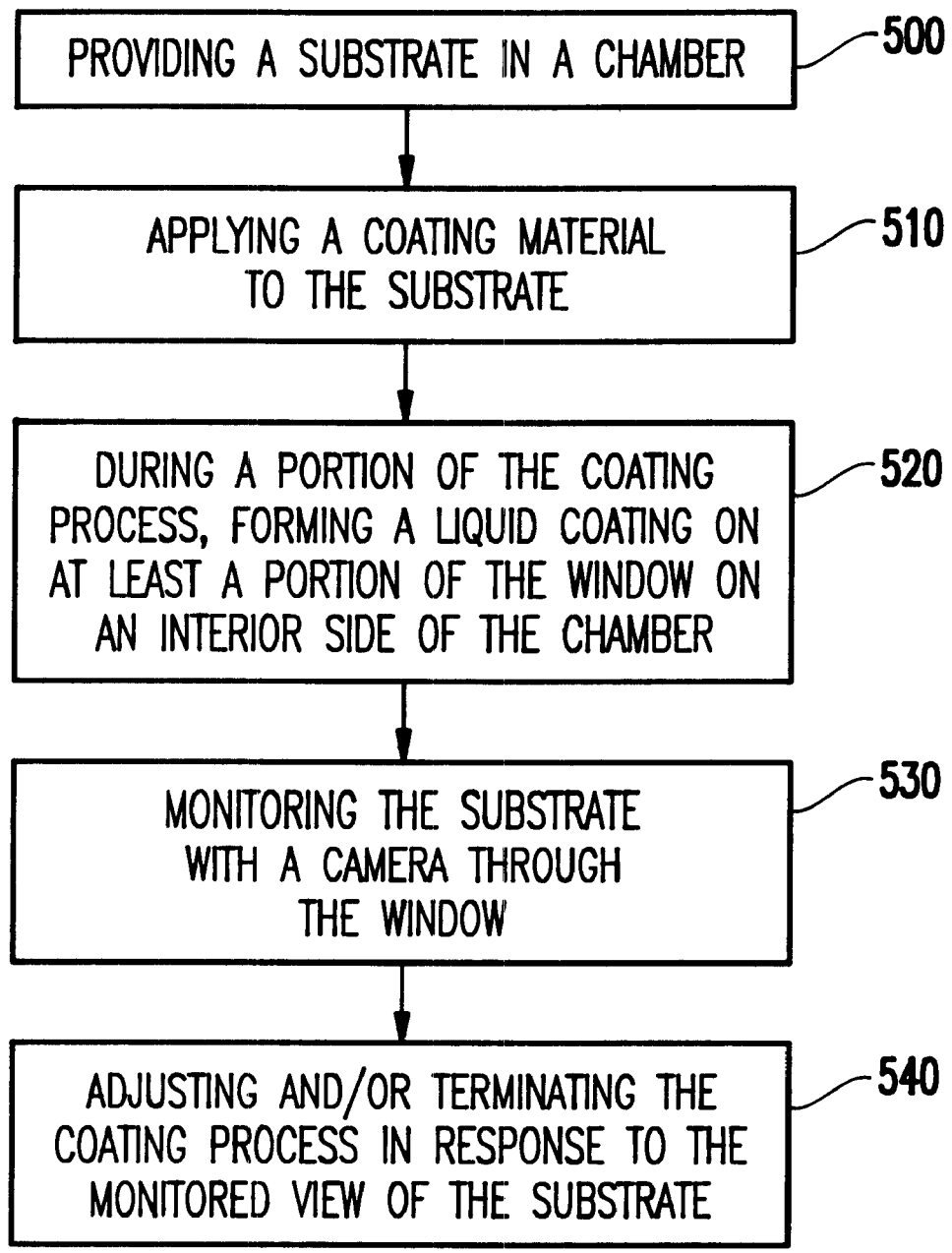
FIG. 10 is a flow diagram illustrating a preferred method of the invention.

FIG. 10 details a methodology in which the present invention may operate. Here, the method for improving the coating on a substrate (115, 215, 315) comprises first providing 500 the substrate (115, 215, 315) in a chamber (105, 205, 305), wherein the chamber (105, 205, 305) has a wall (110, 210, 310), and a window (120, 220, 320) disposed in the wall (110, 210, 310). Second, a coating material is applied 510 to the substrate (115, 215, 315). Third, during at least a portion of the step of applying a coating material to the substrate (115, 215, 315), a liquid coating is formed 520 on at least a portion of the window (120, 220, 320) on an interior side of the chamber (105, 205, 305). Additionally, the substrate (115, 215, 315) rotates during the coating process. A camera (131) monitors 530 the substrate (115, 215, 315) through the window (120, 220, 320) of the chamber (105, 205, 305), wherein the camera (131) is positioned outside the window (120, 220, 320) of the chamber (105, 205, 305). Furthermore, the coating process may be adjusted and/or terminated 540 in response to the monitoring of the substrate (115, 215, 315). As shown in the various embodiments, the chamber (105, 205, 305) is preferably adapted to house the window (120, 220, 320) in multiple configurations. Additionally, the window coating material comprises optical quality materials with suitable chemical and physical properties for the environment, which they are exposed to in their use. Examples of typical materials are $SiO_2$, Pyrex™, transparent $Al_2O_3$, MgO, $CaF_2$, and other transparent glasses, chemically resistant transparent plastics such as thin films of Teflon® (sold by E. I. du Pont de Nemours and Company), or polyethylene or optical coatings of chemically resistant films on a less chemically resistant window (for example MgO on a plastic window).

Often, spin dynamics restrict the physical design of the spin containment bowl. FIGS. 1–9 illustrate the flexibility of the present design and illustrates that the window may be constructed such that some of the edge and contour (total wafer) regions of the wafer can be observed.

The advantages of the structural embodiments of the present invention include the ease of laminar flow for the optical window and the avoidance of turbulence on the wafer coating. An advantage of the first and third embodiments is the ease of manufacturing of the chamber. Moreover, the advantages of the second and third embodiments include the generally vertical laminar flow of the solvent, thereby allowing for a greater flexibility in the type of solvents used, including higher viscous fluids, if desired.

There are several benefits inherent in the present invention. For example, the present invention minimizes the manual observation requirement by using a camera. Thus, every wafer can be inspected. This, in turn, minimizes the number of poorly coated wafers. The unique configuration of the window provides for an easy and optimum observation of the wafers. The present invention effectively multiplies the manpower available for this operation without increasing the amount of manpower needed. Also, the wafer is capable of being observed immediately after processing, and most importantly, during processing. Real time feedback minimizes multiple poor wafers with the same problems. Furthermore, the present invention enhances the assurance that all defects are found, and more importantly, those which are found are correctable.

The wet window is unique and beneficial in that it prevents interference with image collection by removing the dispense solution buildup on the window, which would ordinarily block the view of the camera. Generally, the present invention provides for less product loss, because typically some defective films simply cannot be reworked. However, because the present invention can catch the defects at an early stage in the processing, the defects are curable, and can be cured much easier than in other techniques.

While the invention has been described in terms of preferred embodiments, those skilled in the art will recognize that the invention can be practiced with modification within the spirit and scope of the appended claims.

What is claimed is:

1. An apparatus for monitoring a spin-on coating process on a substrate, said apparatus comprising:
    a chamber in which said substrate is positioned;
    a supply of a coating material for coating said substrate in said chamber;
    a transparent window in a wall of said chamber, said window being non-parallel with the position of said substrate in said chamber; and
    a supply of a liquid solvent for coating at least a portion of said window on an interior side of said chamber.

2. The apparatus of claim 1, wherein said chamber is adapted to house said window at multiple angles.

3. The apparatus of claim 1, further comprising an optical detector.

4. The apparatus of claim 3, wherein said window is adapted to provide optical access of said substrate for said optical detector.

5. The apparatus of claim 4, wherein said optical detector is positioned outside said window of said chamber.

6. The apparatus of claim 1, further comprising a dispenser adapted to flow said solvent over said window, such that said solvent remains laminar over said window.

7. A system for monitoring a spin-on coating process on a wafer, said system comprising:
    a chamber in which said wafer is positioned;
    coating material for coating said wafer in said chamber;
    a wall of said chamber, wherein said wall comprises a transparent window, said window being non-parallel with the position of said wafer in said chamber; and
    liquid solvent for coating at least a portion of said window on an interior side of said chamber, wherein said chamber is adapted to house said window at multiple angles.

8. The system of claim 7, further comprising an optical detector.

9. The system of claim 8, wherein said window is adapted to provide optical access of said wafer for said optical detector.

10. The system of claim 9, wherein said optical detector is positioned outside said window of said chamber.

11. The system of claim 7, further comprising a dispenser adapted to flow said solvent over said window, such that said solvent remains laminar over said window.

12. A method for monitoring a spin-on coating process on a substrate, said method comprising;
    providing said substrate in a chamber, said chamber having a transparent window in a wall of said chamber, said window being non-parallel with a position of said substrate in said chamber;
    spin-on applying a coating material to said substrates, and during at least a portion of said step of spin-on applying, forming a liquid solvent coating on at least a portion of said window on an interior side of said chamber.

13. The method of claim 12, wherein said substrate rotates during said applying process.

14. The method of claim 12, wherein an optical detector monitors said substrate through said window of said chamber.

15. The method of claim 14, wherein said optical detector is positioned outside said window of said chamber.

16. The method of claim 12, wherein said substrate is a wafer.

17. The method of claim 12, wherein said spin-on applying is terminated in response to said monitoring of said substrate.

18. The method of claim 12, wherein said chamber is adapted to house said window at multiple angles.

19. The method of claim 12, wherein said liquid solvent comprises a solvent selected from the group consisting of propylene glycol methyl ether acetate, cyclohexanol, gamma butero lactone, mesitylene, and combinations thereof.

* * * * *